(12) United States Patent
Worrell et al.

(10) Patent No.: US 10,646,270 B2
(45) Date of Patent: May 12, 2020

(54) SURGICAL INSTRUMENT WITH ARTICULATING PORTION

(71) Applicant: Ethicon Endo-Surgery, LLC, Guaynabo, PR (US)

(72) Inventors: Barry Worrell, Centerville, OH (US); Gregory A. Trees, Cincinnati, OH (US); William Douglas Shaw, Jr., Cincinnati, OH (US); Kevin M. Montgomery, Camden, OH (US)

(73) Assignee: Ethicon LLC, Guaynabo, PR (US)

( * ) Notice: Subject to any disclaimer, the term of this patent is extended or adjusted under 35 U.S.C. 154(b) by 390 days.

(21) Appl. No.: 15/368,385

(22) Filed: Dec. 2, 2016

(65) Prior Publication Data

US 2018/0153573 A1    Jun. 7, 2018

(51) Int. Cl.
 *A61B 18/00* (2006.01)
 *A61B 18/14* (2006.01)
 (Continued)

(52) U.S. Cl.
 CPC .. *A61B 18/1445* (2013.01); *A61B 17/320092* (2013.01); *A61B 2017/00026* (2013.01); *A61B 2017/00039* (2013.01); *A61B 2017/00088* (2013.01); *A61B 2017/00119* (2013.01); *A61B 2017/00305* (2013.01);
 (Continued)

(58) Field of Classification Search
 CPC . A61B 17/320092; A61B 17/28; A61B 17/29; A61B 17/22031; A61B 17/2909; A61B 17/30; A61B 2017/320093; A61B 2017/320094; A61B 2017/320095; A61B 2017/320097; A61B 2017/2926; A61B 2017/00039; A61B 2017/00026; A61B 2017/00088; A61B 2017/00119; A61B 2017/00305; A61B 2017/00318; A61B 2017/00862; A61B 2017/2927; A61B 18/1445; A61B 2018/00297; A61B 2018/00601; A61B 2018/0063; A61B 2018/00815; A61B 2018/00875; A61B 2018/1445; A61M 25/0133; A61M 25/0105

See application file for complete search history.

(56) References Cited

U.S. PATENT DOCUMENTS 6,595,958 B1 * 7/2003 Mickley ............ A61M 25/0041
 604/164.01
9,161,803 B2  10/2015 Yates et al.
(Continued)

*Primary Examiner* — Tan-Uyen T Ho
*Assistant Examiner* — Erich G Herbermann
(74) *Attorney, Agent, or Firm* — Mintz Levin Cohn Ferris Glovsky and Popeo, P.C.

(57) ABSTRACT

Surgical instruments having articulating portions or joints are described herein. In one embodiment, a surgical instrument can include a distal end effector, a proximal actuating portion, and an articulating portion disposed between the end effector and the actuating portion. The articulating portion can include an inner component formed of a first material and an outer component formed of a second material, wherein a modulus of elasticity of the first material is higher than a modulus of elasticity of the second material. Such an instrument can be less complex and less expensive than known articulation mechanisms while providing similar capabilities.

20 Claims, 13 Drawing Sheets

(51) Int. Cl.
*A61B 17/32* (2006.01)
*A61B 17/00* (2006.01)
*A61B 17/29* (2006.01)

(52) U.S. Cl.
CPC ............... *A61B 2017/00318* (2013.01); *A61B 2017/00862* (2013.01); *A61B 2017/2927* (2013.01); *A61B 2017/320094* (2017.08); *A61B 2017/320095* (2017.08); *A61B 2018/0063* (2013.01); *A61B 2018/00297* (2013.01); *A61B 2018/00601* (2013.01); *A61B 2018/00815* (2013.01); *A61B 2018/00875* (2013.01); *A61B 2018/1455* (2013.01)

(56) References Cited

U.S. PATENT DOCUMENTS

| | | | |
|---|---|---|---|
| 2007/0078459 A1* | 4/2007 | Johnson | A61B 17/29 606/51 |
| 2011/0184459 A1* | 7/2011 | Malkowski | A61B 17/29 606/206 |
| 2012/0078139 A1 | 3/2012 | Aldridge et al. | |
| 2012/0078247 A1 | 3/2012 | Worrell et al. | |
| 2012/0078248 A1* | 3/2012 | Worrell | A61B 18/1445 606/45 |
| 2013/0281924 A1* | 10/2013 | Shellenberger | A61B 17/00234 604/95.01 |
| 2014/0088497 A1* | 3/2014 | Campbell | A61M 25/0136 604/95.04 |
| 2015/0209573 A1 | 7/2015 | Hibner et al. | |

* cited by examiner

SURGICAL INSTRUMENT WITH ARTICULATING PORTION

FIELD

This disclosure relates generally to surgical instruments and, more particularly, to such instruments that include articulating portions to allow relative position changes between portions of the instrument.

BACKGROUND

A variety of surgical instruments are employed in various open, endoscopic, and laparoscopic surgeries. One group of such instruments is utilized to manipulate tissue, seal tissue, and/or transect tissue. These instruments can include a distal end effector having opposed jaw members that move relative to one another to grasp tissue therebetween. Certain of these instruments can also include a cutting mechanism that can be advanced through the grasped tissue to transect it. Electrical or other energy can also be delivered to the grasped tissue to seal the tissue prior to, or concurrent with, transection. For example, electrical energy can be applied to the grasped tissue by various mono-polar and bi-polar radio frequency (RF) electrodes or other energy delivery structures coupled to the jaw members. In other embodiments, ultrasonic energy can be applied to tissue by an oscillating element to effect tissue sealing and transection.

These surgical instruments often include a proximal actuating portion from which the distal end effector can be controlled. The proximal actuating portion can include a plurality of triggers or other control mechanisms to control the various functions of the instrument. For example, a first trigger can control the opening or closing of the jaw members to grasp tissue, while a second trigger can control the operation of a cutting mechanism and/or the delivery of energy to seal tissue. In use, a user can actuate the first trigger and hold or latch it in an actuated or closed position to securely grasp and compress tissue between the first and second jaw members, then the user can actuate the second trigger to transect and/or seal the tissue.

Certain surgical instruments can also include an articulating portion that allows the end effector to be moved relative to the actuating portion. For example, an articulating portion can be included in some instruments along the length of a shaft that connects the distal end effector to the proximal actuating portion. The articulating portion can permit the end effector to be positioned such that a longitudinal axis of the end effector is transverse, or non-parallel, to a longitudinal axis of the actuating portion or the shaft extending therefrom. The ability to articulate the end effector relative to the actuating portion can be valuable, as it can permit the instrument to access tissue and perform surgical operations that might not otherwise be possible, or at least might be more difficult or physically awkward to perform with a straight shaft instrument.

A number of different configurations for articulating portions are known in the art, but often include associated disadvantages. For example, some known designs employ a series of segmented sections wherein each section has a certain degree of freedom to move relative to an adjacent section. Utilizing one or more of these sections can allow for varying degrees of articulation. Unfortunately, known segmented articulating portions often lack desired levels of stiffness when subjected to compressive axial loads. For example, if a user attempts to push such an instrument through tissue or a tight opening, prod tissue, dissect tissue, etc., resistance can cause undesirable articulation of the end effector. Moreover, known segmented designs often articulate in unpredictable manners because each adjacent segment is able to articulate in a plurality of directions, e.g., via a plurality of ball-and-socket type interfaces.

Furthermore, some known articulating portion designs include one or more openings or other features formed on an outer surface of the articulating portion. These openings or other features can include, for example, relief slots or other features that can aid articulation. Such features can also have undesired effects, however, including capturing tissue and other debris that can complicate procedures, or allow fluid ingress into the instrument.

Still further, known articulating portion designs can be complex multi-component assemblies. Such designs can have increased manufacturing costs associated therewith and, in the event of device disassembly for sterilization or reuse, can be more costly to process.

Accordingly, there is a need for surgical instruments with improved articulating joints or portions. More particularly, there is a need for such instruments having less complex articulating portions that can match or exceed the performance capabilities of known devices.

SUMMARY

The present disclosure generally provides surgical instruments with articulating portions that address the above-described drawbacks. Articulating portions of the instruments described herein can include monolithic components, e.g., extrusions, of materials having elasticities selected to achieve desired performance. In one embodiment, for example, an articulating portion can include an inner component formed of a first material and an outer component formed of a second material that surrounds the inner component. Such materials can, in some embodiments, be formed by a co-extrusion process. The first material and the second material can have differing moduli of elasticity such that the materials together form an articulating portion that is substantially rigid and straight but can be elastically bent via an articulation mechanism, such as a proximally and distally translating band, rod, etc. Alternatively, a single material of a selected hardness and/or elasticity can be utilized to form the articulating portion.

The surgical instruments described herein can have a number of advantages over other designs. For example, utilizing articulating portions that can be extruded using known techniques can reduce the manufacturing cost and complexity when compared to, e.g., segmented articulating portions. Moreover, the articulating portions described herein can provide increased resistance to unintentional articulation during, e.g., compressive axial loading, while still allowing elastic deformation during articulation. Still further, the articulating portions described herein can include an uninterrupted outer surface that can reduce potential for unintentionally catching or trapping tissue. The outer surface can also be sealed to prevent fluid or debris ingress into the instrument.

In one aspect, a surgical instrument is provided that includes a distal end effector, a proximal actuating portion, and an articulating portion disposed between the end effector and the actuating portion. The articulating portion can have an inner component formed of a first material and an outer component formed of a second material. Further, a modulus of elasticity of the first material can be higher than a modulus of elasticity of the second material and the inner component can include a lumen formed therein.

The instruments and methods described herein can have a number of additional features and/or variations, all of which are within the scope of the present disclosure. In some embodiments, for example, the instrument can also include an articulation control element that extends through the lumen of the articulating portion and is coupled to the distal end effector and proximal actuating portion.

In other embodiments, the instrument can further include a cutting element disposed within the lumen of the articulating portion. The cutting element can be configured in some embodiments to translate proximally and distally relative to the articulating portion. The cutting element can include a tapered distal end that can sever tissue and, in some embodiments, can be configured to pass through tissue via ultrasonic vibration.

The distal end effector can include first and second jaw members in some embodiments. The first and second jaw members can be movable relative to one another between an open position and a closed position to clamp tissue therebetween. In some embodiments, the first and second jaw members can include various features formed thereon, such as protrusions, recesses, teeth, ridges, etc. that can be configured to facilitate grasping of tissue abutting against the first and second jaw members. Further, the first and second jaw members can include one or more electrodes formed thereon or coupled thereto such that energy, such as radio frequency (RF) electrical energy, can be delivered to tissue grasped by the first and second jaw members.

While components, such as the articulation control element and the cutting element, can reside in a single lumen in some embodiments, in other embodiments the articulating portion can include a plurality of lumens formed therein. For example, the inner component can include at least a first of the plurality of lumens configured to receive a cutting element and at least a second of the plurality of lumens configured to receive an articulation control element. In some embodiments, the inner component can include at least a first of the plurality of lumens formed therein and the outer component can include at least a second of the plurality of lumens formed therein. For example, the inner component can include at least one lumen configured to receive a cutting element and the outer component can include at least one lumen configured to receive an articulation control element.

In still other embodiments, the outer component can have an uninterrupted outer surface. An uninterrupted outer surface can prevent the articulation portion from catching on tissue or other materials during use and can prevent ingress of fluids into the instrument.

In some embodiments, it can be advantageous for the first material to have different properties from the second material. For example, the first and second materials can have different moduli of elasticity. By way of further example, in some embodiments a modulus of elasticity of the first material that forms the inner component can be approximately in the range of about 100 ksi (about 690 MPa) and about 600 ksi (about 4.13 GPa). In some embodiments, a modulus of elasticity of the second material that forms the outer component can be approximately in the range of about 1 ksi (about 6.9 MPa) and about 100 ksi (about 690 MPa).

Any of the outer and inner components can also be configured to have a variety of other mechanical properties. For example, in some embodiments any of the inner component and the outer component can be chosen to withstand peak strains of about 10% to about 200%.

The inner and outer components of the articulation portion can be formed from a variety of materials. In some embodiments, the first material that forms the inner component can be any of nylon, polyetherimide, and polycarbonate. The second material that forms the outer component can be any of silicone, urethane, and polytetrafluoroethylene. This listing of materials is not exhaustive, however, and there are other known materials that could be utilized in forming the inner and outer components of the articulation portion.

In another aspect, a surgical instrument is provided that can include a distal end effector, a proximal actuating portion, and a plurality of articulation control elements that are coupled to the end effector and the actuating portion. The instrument can further include a cutting element coupled to the end effector and the actuating portion, as well as an articulating portion formed of a single material that is disposed between the end effector and the actuating portion. The articulating portion can include a plurality of lumens that contain the plurality of articulation control elements and the cutting element. Further, the plurality of articulation control elements can be configured to carry all tensile loads created by the cutting element such that no tensile load is carried by the articulating portion.

As with the instrument described above, a number of variations and additional features are possible. For example, in some embodiments the plurality of lumens formed in the articulating portion can each have a shape and a cross-sectional area that are substantially the same as a shape and a cross-sectional area of one of the plurality of articulation control elements or the cutting element.

In some embodiments, the single material that forms the articulating portion can have a Shore A durometer approximately in the range of about 70 and about 80. In other embodiments, the plurality of articulation elements can be oriented to extend perpendicularly from a proximal end of the end effector. Still further, in some embodiments the plurality of articulation control elements can include two articulation control elements positioned on opposite sides of the cutting element.

Any of the features or variations described above can be applied to any particular aspect or embodiment of the disclosure in a number of different combinations. The absence of explicit recitation of any particular combination is due solely to the avoidance of repetition in this summary.

DETAILED DESCRIPTION

Figure 1:
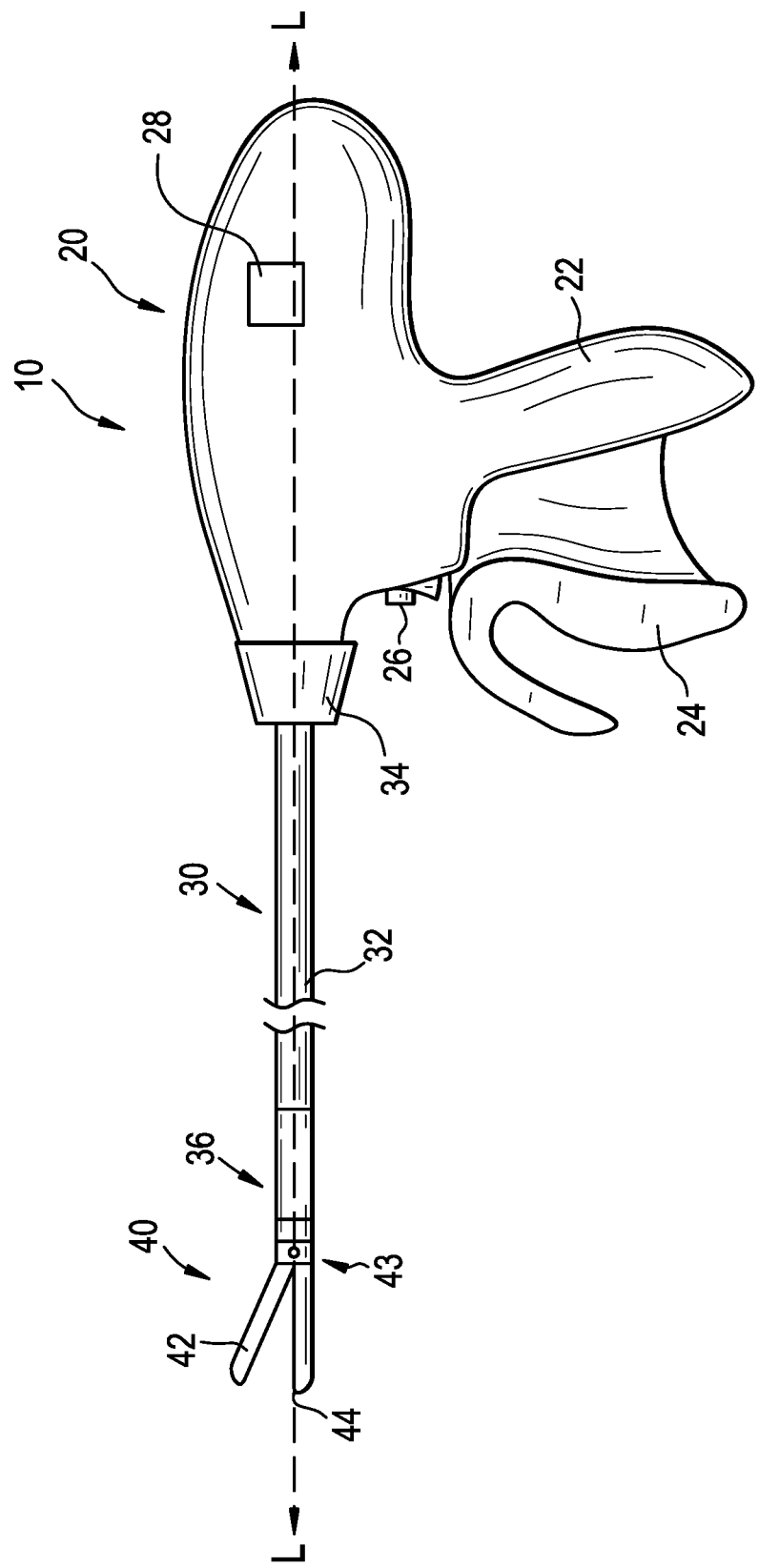
FIG. 1 is a side view schematic of one embodiment of a surgical instrument including an articulating portion.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present application. To the extent that features are described herein as being a "first feature" or a "second feature," such numerical ordering is generally arbitrary, and thus such numbering can be interchangeable.

Additionally, to the extent that linear or circular dimensions are used in the description of the disclosed instruments and methods, such dimensions are not intended to limit the types of shapes that can be used in conjunction with such instruments and methods. A person skilled in the art will recognize that an equivalent to such linear and circular dimensions can easily be determined for any geometric shape. Still further, sizes and shapes of the instruments, and the components thereof, can depend at least on the anatomy of the subject in which the instruments will be used, the size and shape of components with which the instruments will be used, and the methods and procedures in which the instruments will be used.

Surgical instruments and methods are described herein that provide improved articulating portions. FIGS. 1-4 show one embodiment of an electrosurgical instrument 10 that can cut tissue and seal or weld tissue (e.g., a blood vessel, etc.) substantially simultaneously. The electrosurgical instrument 10 can include an actuating portion 20, a shaft 30 extending distally from the actuating portion 20, and an end effector 40 disposed at a distal end of the shaft 30. The actuating portion 20 can have a variety of forms and can be configured to interface with a human operator, e.g., a surgeon, or another instrument, e.g., a surgical robot. As in the illustrated embodiment, the actuating portion 20 can include a pistol grip 22, a first trigger 24, a second trigger 26, and an articulation control 28. The first trigger 24 can be pivotable toward and away from the pistol grip 22 to selectively actuate first and second jaws 42, 44 of the end effector 40, as described in greater detail below. The second trigger 26, illustrated as a button, can be operable to selectively activate RF circuitry that is in communication with the end effector 40, as also described in greater detail below. The pistol grip 22, first trigger 24, and second trigger 26 can be modified, substituted, supplemented, etc. in any suitable way, and descriptions of such components herein are merely illustrative. The articulation control 28 can be operable to selectively control articulating portion 36 that is coupled to the shaft 30, as described in greater detail below. The articulation control 28 can have a variety of configurations, including buttons, slides, levers, etc. Further, the articulation control 28 can be configured to merely lock and unlock the articulating portion 36, thereby permitting passive articulation (in which a user applies an external force to the end effector 40 to cause movement thereof relative to the actuating portion 20), or the articulation control 28 can be coupled to one or more components (e.g., a motor, gear, etc.) that can actively cause movement of the articulating portion.

The shaft 30 can include an outer sheath 32 and can be coupled to the articulating portion 36. The articulating portion 36 can be operable to selectively position the end effector 40 at various angles relative to the longitudinal axis L defined by the sheath 32. Various examples of the articulating portion 36 and other components of the shaft 30 are described in greater detail below, and further examples will be apparent to those of ordinary skill in the art in view of the teachings herein. For instance, it should be understood that various components that are operable to actuate the articulating portion 36 can extend through the interior of the sheath 32. In some embodiments, the shaft 30 can also be rotatable about the longitudinal axis L defined by the sheath 32, relative to the actuating portion 20, via a knob 34. Such rotation can provide rotation of the end effector 40 and the shaft 30 unitarily. In other embodiments, the knob 34 can be operable to rotate the end effector 40 without rotating any portion of the shaft 30 that is proximal to the articulating portion 36. As another merely illustrative example, the electrosurgical instrument 10 can include a first rotation control that controls rotation of the shaft 30 and the end effector 40 as a single unit; and another rotation control that controls rotation of the end effector 40 without rotating any portion of the shaft 30 that is proximal to the articulating portion 36. Other suitable configurations for enabling rotation will be apparent to those of ordinary skill in the art in view of the teachings herein. Of course, rotation features can be omitted in some embodiments.

As noted above, in some embodiments the end effector 40 can include a first jaw 42 and a second jaw 44. Depending upon the particular embodiment, both the first and second jaws 42, 44 can move relative to one another or, as in the illustrated embodiment, the second jaw 44 can be substantially fixed relative to the shaft 30, while the first jaw 42 can pivot relative to the shaft 30 toward and away from the second jaw 42. In some embodiments, one or more actuators, such as rods, cables, bands, etc., can extend through the sheath 32 and be joined with the first jaw 42 at a pivot coupling 43, such that longitudinal or rotational movement of the actuator rods, cables, bands, etc. through the shaft 30 can provide pivoting of the first jaw 42 relative to the shaft 30 and relative to the second jaw 44. Of course, the first and second jaws 42, 44 can instead have any other suitable kind of movement and can be actuated in any other suitable fashion.

Figure 2:
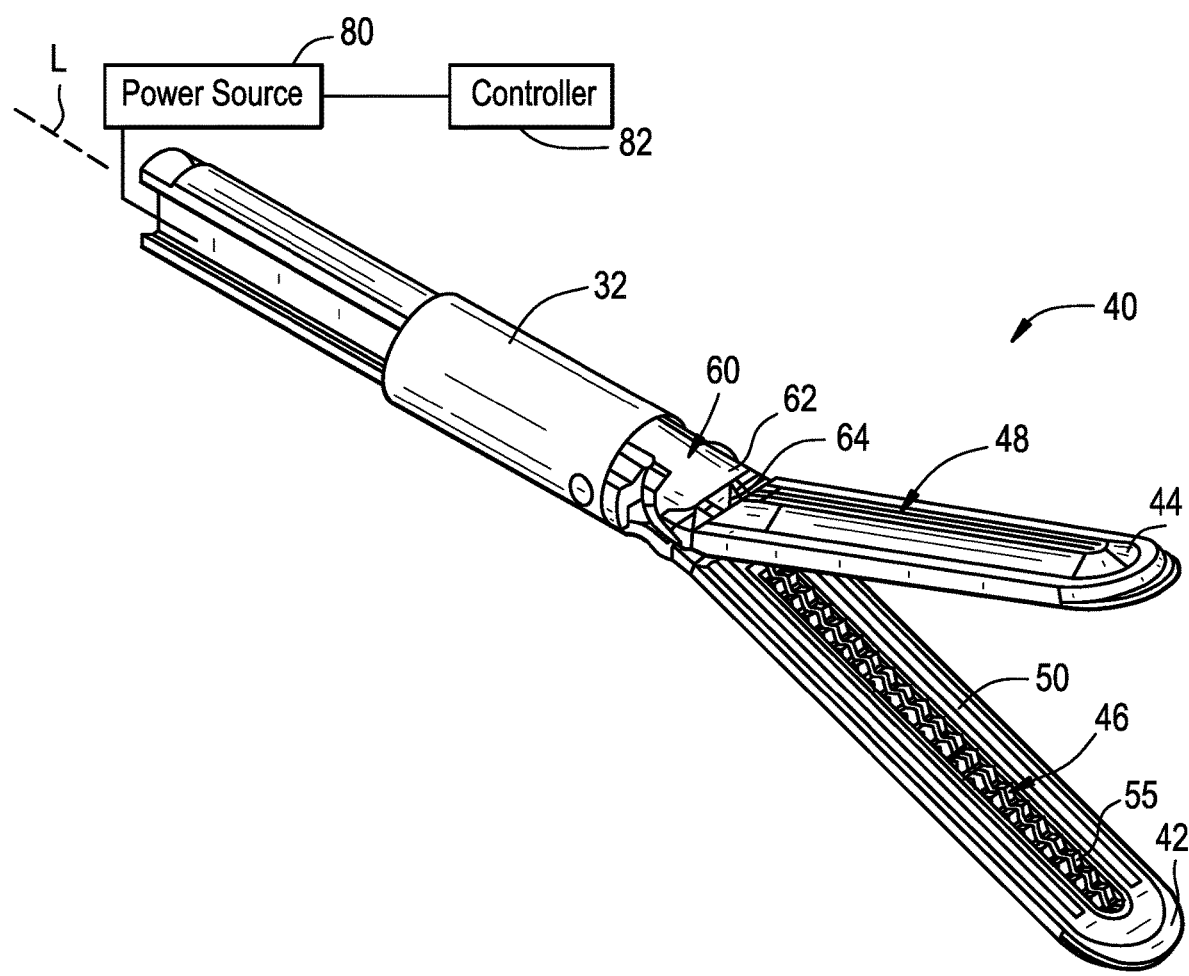
FIG. 2 is a perspective partial cutaway view of an end effector of the instrument of FIG. 1.
Figure 3:
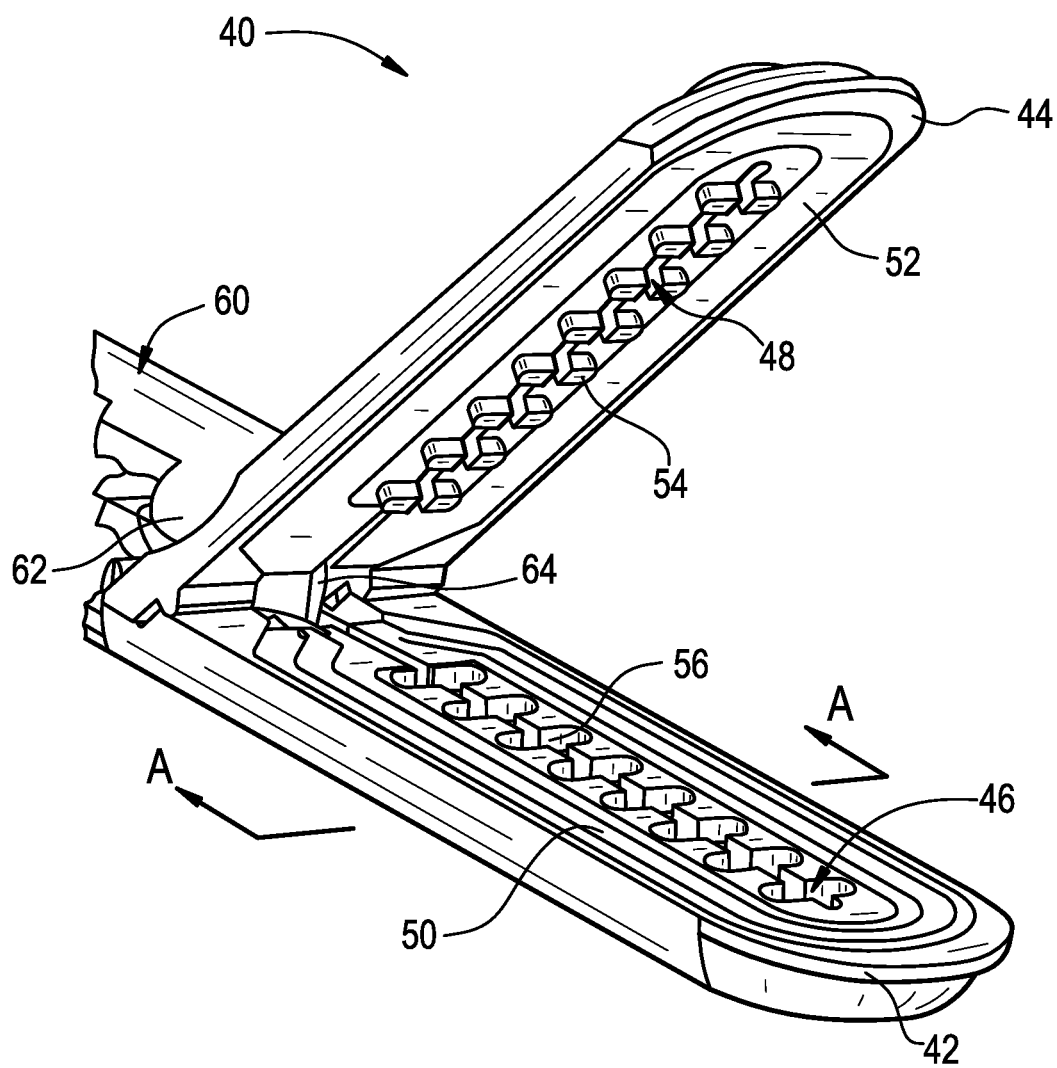
FIG. 3 is a detail view of an end effector of the instrument of FIG. 1 in an open position.
Figure 4:
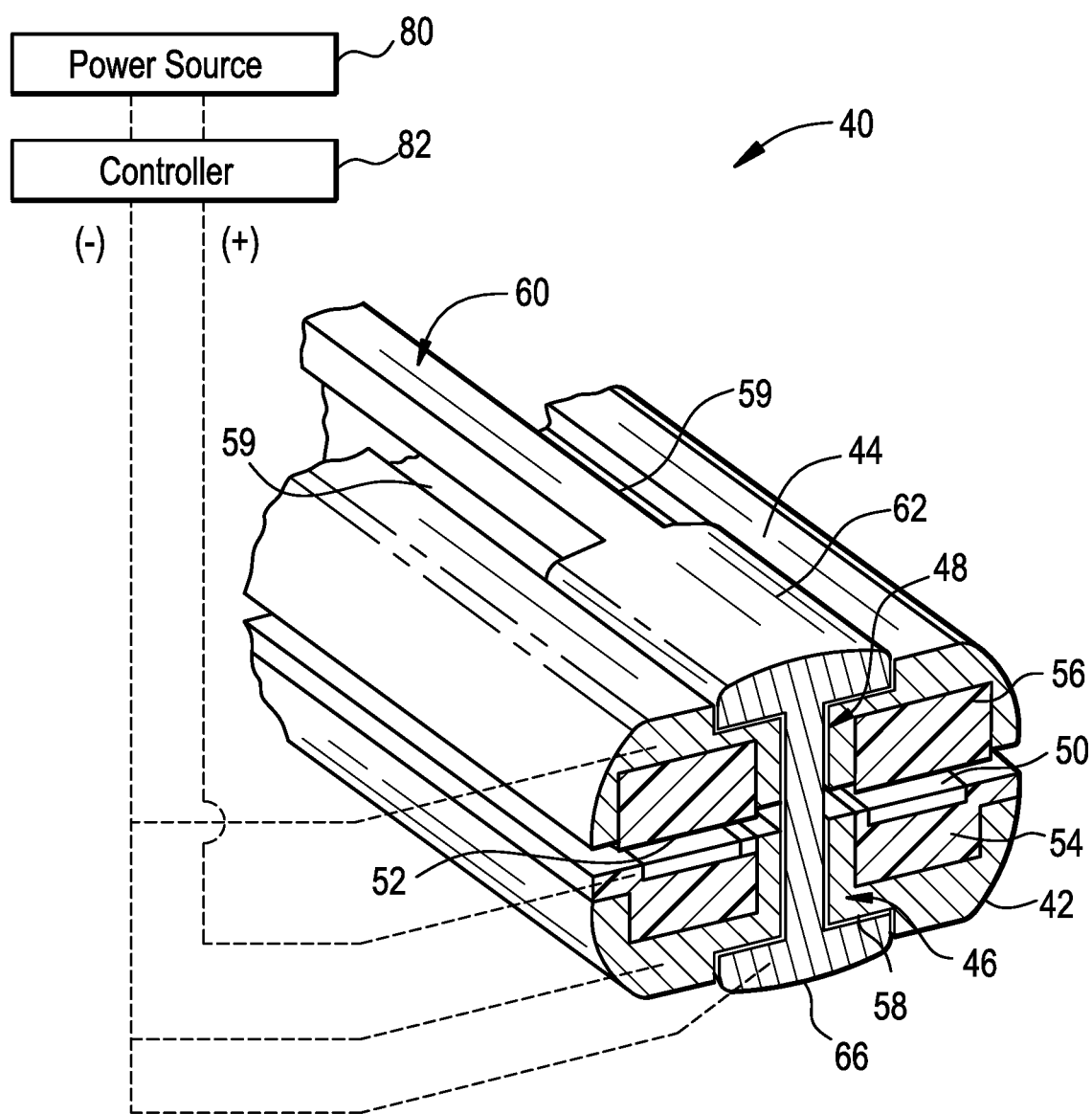
FIG. 4 is a perspective cross-sectional view, taken along the line A-A shown in FIG. 3, of the end effector of the instrument of FIG. 1 in a closed position.

As best seen in FIGS. 2-4, the first jaw 42 can define a longitudinally extending elongate slot 46; while the second jaw 44 can define a longitudinally extending elongate slot 48. In addition, the top side of the first jaw 42 can include a first electrode surface 50; while the underside of the second jaw 44 can include a second electrode surface 52. The electrode surfaces 50, 52 can be in communication with an electrical source 80 via one or more conductors (not shown) that can extend along the length of the shaft 30. The electrical source 80 can be operable to deliver radio frequency (RF) or other electrical energy to the first electrode surface 50 at a first polarity and to the second electrode surface 52 at a second (opposite) polarity, such that RF current can flow between the electrode surfaces 50, 52 and thereby through tissue captured between the first and second jaws 42, 44. In some embodiments, a firing beam 60 can serve as an electrical conductor that can cooperate with the electrode surfaces 50, 52 (e.g., as a ground return) for delivery of bipolar RF energy to tissue captured between the first and second jaws 42, 44. The electrical source 80 can be external to the electrosurgical instrument 10 or can be integral therewith (e.g., in the actuating portion 20, etc.). A controller 82 can regulate delivery of power from the electrical source 80 to the electrode surfaces 50, 52. The controller 82 can also be external to the electrosurgical instrument 10 or can be integral therewith (e.g., in the actuating portion 20, etc.). The electrode surfaces 50, 52 can also be provided in a variety of alternative locations, configurations, and relationships.

As shown in FIG. 4, the lower side of the first jaw 42 can include a longitudinally extending recess 58 adjacent to the slot 46, while the upper side of the second jaw 44 can include a longitudinally extending recess 59 adjacent to the slot 48. FIG. 2 shows the upper side of the first jaw 42 including a plurality of teeth serrations 55. The lower side of the second jaw 44 can include complementary serrations that nest with the serrations 55 to enhance gripping of tissue captured between the first and second jaws 42, 44 without necessarily tearing the tissue. In various embodiments, the serrations can have any other suitable form, e.g., any pattern of complementary recesses, protrusions, or other features formed on or in the surfaces of the first and second jaws 42, 44, or such features can be omitted altogether. In some embodiments, the serrations 55 can be formed from an electrically non-conductive, or insulative, material, such as a plastic, a glass, and/or a ceramic, for example, and can include a treatment, such as polytetrafluoroethylene, a lubricant, or some other treatment, to substantially prevent tissue from sticking to the first and second jaws 42, 44 during use.

In certain embodiments, the distal end effector 40 and the shaft 30 can be sized and configured to fit through trocars having various inner diameters, such that the electrosurgical instrument 10 can be used in minimally invasive surgery. Of course, the electrosurgical instrument 10 can also be used in open procedures if desired. By way of example only, with the first and second jaws 42, 44 in a closed position, the shaft 30 and the end effector 40 can have an outer diameter of approximately 5 mm. Alternatively, the shaft 30 and the end effector 40 can have any other suitable outer diameter (e.g., between approximately 2 mm and approximately 20 mm, etc.).

As another merely illustrative variation, either or both of the first and second jaws 42, 44 can include at least one port, passageway, conduit, and/or other feature operable to draw steam, smoke, and/or other gases, vapors, etc. from the surgical site. Such a feature can be in communication with a source of suction, such as an external source or a source within the actuating portion 20, etc. In addition, the end effector 40 can include one or more tissue cooling features (not shown) that can reduce the degree or extent of excess thermal damage caused by the end effector 40 when the electrode surfaces 50, 52 are activated. Various suitable forms that such cooling features may take are known.

In some embodiments, the end effector 40 can include one or more sensors (not shown) that can be configured to sense a variety of parameters at the end effector 40, including but not limited to temperature of adjacent tissue, electrical resistance or impedance of adjacent tissue, voltage across adjacent tissue, force exerted on the first and second jaws 42, 44 by adjacent tissue, etc. By way of example only and as shown in FIGS. 3-4, the end effector 40 can include one or more positive temperature coefficient (PTC) thermistor bodies 54, 56 (e.g., PTC polymer, etc.) located adjacent to the electrodes 50, 52 and/or elsewhere. During use, data from sensors may be communicated to the controller 82 and can be processed by the controller in a variety of ways. By way of example only, the controller 82 can modulate or otherwise change the RF energy being delivered to the electrode surfaces 50, 52 based at least in part on data acquired from one or more sensors at the end effector 40. In addition or alternatively, the controller 82 can alert the user to one or more conditions via an audio, visual, and/or haptic feedback device (e.g., a speaker, lights, a display screen, a vibrating element, etc.) based at least in part on data acquired from one or more sensors at the end effector 40. Certain types of sensors need not necessarily be in communication with the controller 82 and can simply provide a localized effect at the end effector 40. For instance, the PTC thermistor bodies 54, 56 at the end effector 40 can automatically reduce the amount of energy delivery at the electrode surfaces 50, 52 as the temperature of the tissue and/or the end effector 40 increases, thereby reducing the likelihood of overheating. In some embodiments, a PTC thermistor element can be in series with the power source 80 and the electrode surfaces 50, 52 and the PTC thermistor can provide an increased impedance (reducing flow of current) in response to temperatures exceeding a threshold. Furthermore, the electrode surfaces 50, 52 can be used as sensors (e.g., to sense tissue impedance, etc.). Any of a variety of other sensors can be incorporated into the electrosurgical instrument 10 and data from such sensors can be utilized in a variety of different manners by the controller 82 or otherwise.

As also seen in FIGS. 2-4, the electrosurgical instrument 10 can include a firing beam 60 that is longitudinally movable along part of the length of the end effector 40. The firing beam 60 can be coaxially positioned within the shaft 30, can extend along the length of the shaft 30, and can translate longitudinally within the shaft 30 (including the articulating portion 36), though it should be understood that the firing beam 60 and the shaft 30 can have any other suitable relationship. The firing beam 60 can include a sharp distal blade 64 integrally formed therein or coupled thereto, thereby making the firing beam effective as a cutting element or mechanism. In some embodiments, this can be the sole purpose of the firing beam 60. In some embodiments, however, the firing beam 60 can also function to exert a force on the first and second jaws 42, 44 to urge them between their open and closed configurations. As in the illustrated embodiment, for example, the firing beam 60 can include an upper flange 62 and a lower flange 66. As best seen in FIG. 4, the distal blade 64 can extend through the slots 46, 48 of the first and second jaws 42, 44, with the upper flange 62 being located above the second jaw 44 in the recess 59 and the lower flange 66 being located below the first jaw 42 in the recess 58. The configuration of the distal blade 64 and the flanges 62, 66 can provide an "I-beam" type of cross section at a distal end of the firing beam 60. While the flanges 62, 66 are shown in the figures extending longitudinally only along a small portion of the length of the firing beam 60, in some embodiments the flanges 62, 66 can extend longitudinally along any suitable length of the firing beam 60. In addition, while the flanges 62, 66 are shown in the figures positioned along the exterior of the first and second jaws 42, 44, the flanges 62, 66 can alternatively be disposed in corresponding slots formed within the first and second jaws 42, 44. For instance, each jaw 42, 44 can define a "T"-shaped slot, with parts of the distal blade 64 being disposed in one vertical portion of each "T"-shaped slot and with the flanges 62, 66 being disposed in the horizontal portions of the "T"-shaped slots. There are a variety of other suitable configurations and relationships that can also be utilized in connection with the teachings provided herein.

The distal blade 64 can be substantially sharp, such that the distal blade will readily sever tissue that is captured between the first and second jaws 42, 44, thereby enabling the firing beam 60 to serve as a cutting element or mechanism for transecting tissue grasped by the first and second jaws 42, 44. The distal blade 64 can also be electrically grounded in some embodiments to provide a return path for RF energy. In some embodiments, the distal blade 64 can serve as an active electrode. In still other embodiments, the firing beam 60 can be configured to oscillate when energized with ultrasonic energy (e.g., harmonic vibrations at approximately 55.5 kHz, etc.). Examples of applying energy are described further in U.S. Pat. Pub. No. 2012/0078139; U.S. Pat. No. 9,161,803; and U.S. Pat. Pub. No. 2015/0209573, the entire contents of which are hereby incorporated by reference.

As discussed, for example, in previously mentioned U.S. Pat. Pub. No. 2012/0078139, RF energy is a form of electrical energy that can be in the frequency range of 300 kHz to 1 MHz. The electrosurgical instrument 10 can be configured to transmit low frequency RF energy through tissue, which causes ionic agitation, or friction, in effect resistive heating, thereby increasing the temperature of the tissue. Because a sharp boundary can be created between treated tissue and surrounding tissue, users of the instrument 10, e.g., surgeons and/or other medical professionals, can operate on the tissue with a high level of precision and control without damaging un-targeted adjacent tissue. The low operating temperatures of RF energy can be useful for removing, shrinking, or sculpting soft tissue while simultaneously sealing blood vessels. RF energy can work particularly well on connective tissue, which is primarily comprised of collagen and shrinks when contacted by heat. Heat generated by current flow from the RF energy through tissue to which the RF energy is applied can seal the tissue, e.g., form hemostatic seals within the tissue and/or between tissues, and can thus be particularly useful for sealing blood vessels, for example. When the instrument 10 includes a cutting element configured to cut tissue clamped between the jaws and is configured to apply energy to tissue clamped between the jaws so as to seal the tissue, the instrument 10 can be configured to separately cut and seal tissue clamped between the jaws or can be configured to simultaneously cut and seal tissue clamped between the jaws.

As noted above, the "I-beam" type of configuration of the firing beam 60 can also provide closure of the first and second jaws 42, 44 as the firing beam is advanced distally. In particular, the flange 62 can urge the second jaw 44 pivotally toward the first jaw 42 as the firing beam 60 is advanced from a proximal position (FIGS. 1-3) to a distal position (FIG. 4) by bearing against the recess 59 formed in the second jaw 44. This closing effect on the first and second jaws 42, 44 by the firing beam 60 can occur before the distal blade 64 reaches tissue captured between the first and second jaws 42, 44 in certain embodiments. Such staggering of encounters by the firing beam 60 can reduce the force required to squeeze a trigger (e.g., the first trigger 24) to actuate the firing beam 60 through a full firing stroke. In other embodiments, staggering the effect of firing beam translation can allow separate triggers to control the processes of grasping and transecting tissue.

In certain embodiments, the flange 62 can be configured to cam against a ramp feature at the proximal end of the second jaw 44 to open the first jaw 42 when the firing beam 60 is retracted to a proximal position and to hold the first jaw 42 open when the firing beam 60 remains at the proximal position. This camming capability can facilitate use of the end effector 40 to separate layers of tissue, i.e., to perform blunt dissections, etc., by forcing the first and second jaws 42, 44 apart from a closed position. In some embodiments, the first and second jaws 42, 44 can be resiliently biased to an open position by a spring or other type of resilient feature. While the first and second jaws 42, 44 can close or open as the firing beam 60 is translated in some embodiments, it should be understood that other embodiments can provide independent movement of the first and second jaws 42, 44 and the firing beam 60. By way of example only, one or more cables, rods, beams, bands, or other features can extend through the shaft 30 to selectively actuate the first and second jaws 42, 44 independently of the firing beam 60. Such jaw actuation features can be separately controlled by a dedicated feature of the actuating portion 20 or can be controlled along with one or more other functions by a single trigger or actuating element. It should also be understood that the firing beam 60 can be resiliently biased to a proximal position, such that the firing beam 60 retracts proximally when a user releases a trigger or other actuating element controlling the advancement of the firing beam.

In an exemplary use, the end effector 40 can be inserted into a patient via a trocar. The articulating portion 36 can be substantially straight when the end effector 40 and part of the shaft 30 are inserted through the trocar. The articulation control 28 can then be manipulated to pivot or flex the articulating portion 36 of the shaft 30 in order to position the end effector 40 at a desired position and orientation relative to an anatomical structure within the patient. One or more layers of tissue of the anatomical structure can be captured between the first and second jaws 42, 44 by squeezing the first trigger 24 toward the pistol grip 22. In some embodiments, captured layers of tissue can be part of the same natural lumen defining an anatomical structure in a patient (e.g., blood vessel, portion of gastrointestinal tract, portion of reproductive system, etc.). For instance, one tissue layer can include the top portion of a blood vessel while the other tissue layer may include the bottom portion of the blood vessel, along the same region of length of the blood vessel (e.g., such that a fluid path through the blood vessel before use of the electrosurgical instrument 10 is perpendicular to the longitudinal axis L defined by the end effector 40, etc.). In other words, the lengths of the first and second jaws 42, 44 can be oriented perpendicular to (or at least generally transverse to) the length of the blood vessel. As noted above, the flanges 62, 66 can cammingly act to pivot the first jaw 42 toward the second jaw 44 when the firing beam 60 is actuated distally by squeezing the first trigger 24 toward the pistol grip 22.

With tissue layers captured between the first and second jaws 42, 44, the firing beam 60 can continue to advance distally as the user squeezes the first trigger 24 or actuates, e.g., the second 26 or another trigger. As the firing beam 60 advances further distally, the distal blade 64 can simultaneously sever the clamped tissue layers, resulting in separated upper layer portions being apposed with respective separated lower layer portions. In some embodiments, this can result in a blood vessel being cut in a direction that is generally transverse to the length of the blood vessel. The presence of the flanges 62, 66 immediately above and below the first and second jaws 42, 44, respectively, can help keep the first and second jaws 42, 44 in a closed and tightly clamped position. In particular, the flanges 62, 66 can help maintain a compressive force between the first and second jaws 42, 44. With severed tissue layer portions being compressed between the first and second jaws 42, 44, the electrode surfaces 50, 52 can be activated to deliver bipolar RF or other electrical energy by the user depressing, e.g., the second trigger 26. In some embodiments, the electrodes 50, 52 can be selectively coupled with the power source 80 (e.g., by the user depressing the second trigger, another button, etc.) such that the electrode surfaces 50, 52 of the first and second jaws 42, 44 can be activated with a common first polarity while the firing beam 60 is activated at a second polarity that is opposite to the first polarity. Thus, a bipolar RF current can flow between the firing beam 60 and the electrode surfaces 50, 52 of the first and second jaws 42, 44, through the compressed regions of severed tissue layer portions. In some embodiments, the electrode surface 50 can have one polarity while the electrode surface 52 and the firing beam 60 can both have the other polarity. Regardless of the particular polarity configuration, RF energy delivered by the power source 80 can ultimately thermally weld the tissue layer portions on one side of the firing beam 60 together and the tissue layer portions on the other side of the firing beam 60 together.

Heat generated by the energy delivery process can denature the collagen within the tissue layer portions and, in cooperation with clamping pressure provided by the first and second jaws 42, 44, the denatured collagen can form a seal within the tissue layer portions. Thus, the severed ends of the natural lumen defining an anatomical structure can be hemostatically sealed shut, such that the severed ends will not leak bodily fluids. In some embodiments, the electrode surfaces 50, 52 can be activated with bipolar RF energy before the firing beam 60 begins to translate distally and, thus, before the tissue is severed. For instance, such timing can be provided in versions where the second trigger 26 serves to control both tissue sealing and transection, or in embodiments wherein the second trigger 26 serves to mechanically prevent full actuation of the first trigger 24 or another trigger that controls tissue transection unless the second trigger is actuated.

While several of the teachings provided herein are described as variations to the electrosurgical instrument 10, it should be understood that various teachings provided herein can also be incorporated into various other types of devices. By way of example only, in addition to being readily incorporated into the electrosurgical instrument 10, various teachings provided herein can be readily incorporated into devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

As noted above, the electrosurgical instrument 10 can include an articulating portion 36, which can be operable to selectively position the end effector 40 at various angles relative to the longitudinal axis L defined by the shaft 30. Several examples of forms that the articulating portion 36 may take are described in greater detail below, while further examples will be apparent to those of ordinary skill in the art in view of the teachings provided herein.

Figure 5:
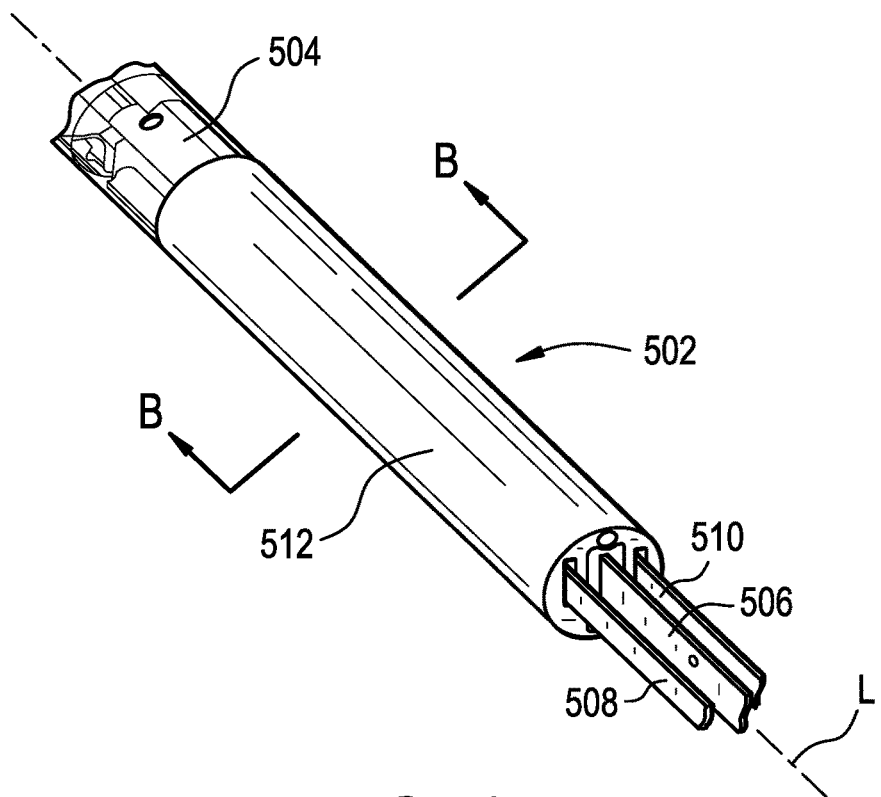
FIG. 5 is a perspective view of an articulating portion of the instrument of FIG. 1.
Figure 6:
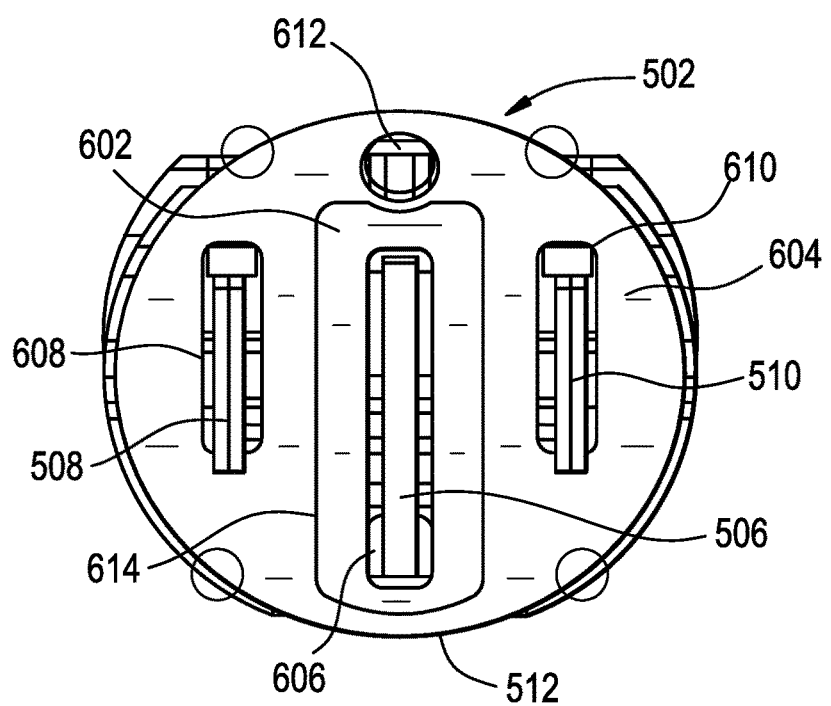
FIG. 6 is a front cross-sectional view, taken along the line B-B shown in FIG. 5, of the articulating portion of the instrument of FIG. 1.

FIGS. 5-6 show one embodiment of an articulating portion 502 according to the teachings provided herein. The articulating portion 502 can be incorporated into the electrosurgical instrument 10 described above or any of a variety of other similar surgical instruments. The articulating portion 502 can be disposed between a rigid shaft 504 (that can extend from a proximal actuating portion not shown in FIGS. 5-6) and an end effector (also not shown in FIGS. 5-6). The articulating portion 502 can be formed from one or more molded or extruded members having desirable stiffness and elasticity to both maintain a straight configuration (e.g., as illustrated in FIG. 5) under compressive axial loading and allow deformation during articulation (e.g., into a curved or bent configuration). As explained in more detail below, the articulating portion 502 can include one or more lumens formed therein that can be configured to receive various components of a surgical instrument. For example, FIG. 5 shows a firing beam/cutting element 506 extending through a centrally-positioned lumen of the articulating portion 502, as well as first and second articulation control bands/elements 508, 510 extending through lumens positioned on either side of the cutting element 506.

FIG. 6 illustrates a more detailed end-view of the articulating portion 502. In this view it can be seen that the articulating portion 502 includes a substantially rectangular inner component 602 and a substantially circular outer component 604. The inner component 602 can be formed from a first material and the outer component 604 can be formed from a second material. Further, the outer component can be configured to surround the inner component such that an outer surface of the inner component is completely enveloped by the outer component. With such a configuration, selecting the first material and the second material can provide the articulating portion 502 with desired levels of resilience and elasticity/deformability. For example, the first material and the second material can be selected such that a modulus of elasticity of the first material is higher than a modulus of elasticity of the second material. A stiffer inner component can provide rigidity and structural support, while a more elastic and deformable outer component can facilitate articulation and accommodate the greater levels of both compressive and tensile deformation encountered at the outermost areas of the articulating portion 502 that are farthest from a central longitudinal axis L of the articulating portion.

As shown in FIG. 6, the articulating portion 502 can include one or more lumens formed therein. In the illustrated embodiment, the inner component 602 includes a first lumen 606 configured to receive the firing beam/cutting element 506. Further, the outer component 604 can include a second lumen 608 and a third lumen 610 that can be configured to receive the first and second articulation control elements 508, 510, respectively. Each of the lumens 606, 608, 610 formed in the inner or outer components 602, 604 of the articulating portion 502 can have varying shapes and cross-sectional areas. In some embodiments, each of the lumens 606, 608, 610 can have a shape and a cross-sectional area that are substantially the same as a shape and a cross-sectional area of the component that is received therewithin.

For example, the first lumen 606 can have a shape and a cross-sectional area that are substantially the same as a shape and a cross-sectional area of the firing beam 506 that is received within the first lumen 606. Similarly, each of the second and third lumens 608, 610 can have a shape and a cross-sectional area that are substantially the same as a shape and a cross-sectional area of the articulation control elements 508, 510 that are received within the second and third lumens, respectively. Substantially matching the shape and size of each lumen with the component received therein can allow for desired relative movement, e.g., proximal and distal translation, while preventing excess play or relative movement in undesired directions that can result from oversized lumens. Of course, there can be embodiments in which a larger lumen is desirable, as described in more detail below.

Any of the inner component 602 and the outer component 604 can also include one or more additional lumens to carry other components of a surgical instrument or provide localization features for connecting to adjacent components. For example, the articulating portion 502 can include a fourth lumen 612 formed in the outer component 604 that can be configured to receive a conductor for delivering electrical energy to one or more energy delivery structures (e.g., electrodes) disposed on, e.g., jaw members of an end effector. Alternatively, the fourth lumen 612 (or an additional lumen) can be configured to receive one or more actuating cables to control, e.g., opening and closing of end effector jaw members in embodiments in which the firing beam 506 functions solely as a cutting element/mechanism.

One advantage of the articulating portion 502 that can be formed from one or more monolithic molded members is that the articulating portion can have an uninterrupted outer surface 512. The uninterrupted outer surface 512 can eliminate ribs, slots, slits, holes, and other features formed on an outer surface of many known articulating portions that can trap tissue during use. For example, some known articulating portions include a plurality of relief slits or slots formed therein that can facilitate articulation, but can also trap tissue therebetween during articulation and other maneuvers. The outer surface 512 can also be sealed against fluid ingress, which is an undesirable effect of the above-described openings formed on many known articulating portions. Accordingly, the articulating portions described herein can match the performance of known designs while presenting a smooth, uninterrupted, and sealed outer surface that prevents fluid or tissue ingress and trapping.

The articulating portion 502 can be formed in a variety of manners, including via a number of methods of molding a variety of materials. In some embodiments, for example, the inner component 602 can be molded from the first material and the second component 604 can be molded from the second material. The two components can then be coupled by inserting the inner component 602 into a central lumen 614 formed in the outer component 604. The central lumen 614 can be sized such that a friction fit holds the two components together. In other embodiments, an adhesive or other chemical bonding process can be used to join the inner and outer components 602, 604 together.

In other embodiments, the outer component 604 can be over-molded on the inner component 602 such that the outer component fits tightly to the inner component. In still other embodiments, the inner and outer components can be extruded to produce any desired length articulating portion. The inner and outer components can be extruded separately and assembled, as described above, or they can be coextruded simultaneously. The articulating portions described herein can be cheaper to produce and more reliable than known articulating portions due to a reduced number of components, design complexity, and manufacturing steps.

A number of different materials can be utilized to form the inner and outer components 602, 604. For example, in some embodiments the first material utilized to form the more rigid inner component 602 can be any of nylon, polycarbonate, polyetherimide (including amorphous thermoplastic polyetherimide such as Ultem™), thermoplastic (including engineered thermoplastic such as Isoplast®), and various other materials. In some embodiments, the second material utilized to form the more flexible outer component 604 can be any of silicone (including soft durometer silicones), urethane, polytetrafluoroethylene (PTEF), and various other materials. In some embodiments, any of the inner component 602 and the outer component 604 can be formed from a plurality of materials representing, e.g., a hybrid or modified form of any of the materials described above.

In some embodiments, the first material and the second material can be selected based on particular mechanical properties of the material. For example, in some embodiments a modulus of elasticity of the inner component 602 and/or the first material can be approximately in the range of about 100 ksi (about 690 MPa) and about 600 ksi (about 4.13 GPa). Further, in certain embodiments a modulus of elasticity of the outer component 604 and/or the second material can be approximately in the range of about 1 ksi (about 6.9 MPa) and about 100 ksi (about 690 MPa). As noted above, it can be desirable to maintain a difference between moduli of elasticity of the first and second materials or inner and outer components 602, 604 such that the inner component is more rigid than the outer component.

Moreover, in some embodiments any of the first material utilized to form the inner component 602 and the second material utilized to form the outer component 604 can be capable of withstanding peak strains of about 10% to about 200%. The ability to withstand such strains can allow the materials utilized to form the articulating portion 502 to bend during articulation without breaking or otherwise failing.

Figure 7:
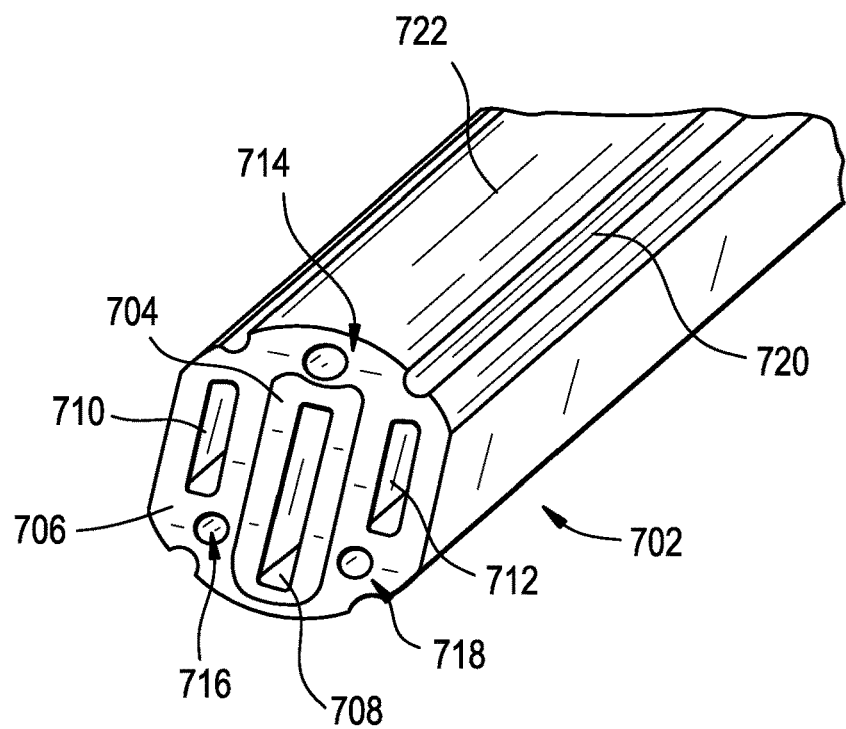
FIG. 7 is a perspective view of another embodiment of an articulating portion of a surgical instrument.

FIG. 7 illustrates an alternative embodiment of an articulating portion 702. Similar to the articulating portion 502 described above, the articulating portion 702 can include a substantially rectangular inner component 704 formed of a first material and an outer component 706 formed of a second material. The first material of the inner component 704 can have a higher modulus of elasticity than the second material of the outer component 706 and the outer component can surround the inner component. The articulating portion 702 can also include one or more lumens formed therein. For example, the inner component 704 can include a first lumen 708 configured to receive a firing beam/cutting element. The outer component 706 can include a second lumen 710 and a third lumen 712 that can be configured to receive first and second articulating control elements extending between a distal end effector and a proximal actuating portion of a surgical instrument. Also shown in FIG. 7 is a fourth lumen 714 configured to receive a conductor or other actuating cable.

The articulating portion 702 of FIG. 7 includes additional lumens 716, 718 as well. The lumens 716, 718 can have a variety of purposes. In some embodiments, for example, the lumens 716, 718 can be configured to carry additional conducting elements, actuating members, data transmission lines, etc., depending upon the particular configuration of the surgical instrument in which the articulating portion 702 is included. In other embodiments, the lumens 716, 718 can be utilized as localization features to ensure alignment between, for example, the articulating portion 702 and adjacent components, such as an end effector or a shaft. By way of further example, an end effector can include one or more protrusions or other features formed on a proximal-facing surface thereof that can be configured to be received within the lumens 716, 718 to ensure proper alignment of the two components during device assembly and to resist relative rotation between the two components during articulation or other use. In some embodiments, the lumens 716, 718 can be formed as bores of a certain depth while in other embodiments the lumens can be through-holes that travel the entire length of the articulating portion 702.

The articulating portion 702 can also include one or more features formed on an outer surface thereof, such as groove 720. Groove 720 can be formed, for example, as a longitudinally extending recess, protrusion, rib, or other structure that can, in some embodiments, either resist or facilitate articulation in a particular direction. For example, including one or more longitudinally extending ribs can add rigidity to the more flexible outer component 706, thereby increasing the resistance of the articulating portion 702 to bending. Groove 720 can also be utilized as a localizing feature, similar to the lumens 716, 718 described above. For example, an end effector configured to abut against a distal end of the articulating portion 702 can include a protrusion formed on a proximal-facing surface thereof that can be configured to be received within the groove 720. The interconnection of such features can ensure proper alignment between the end effector and the articulating portion 702, and can resist relative rotation of the two components during articulation or other use.

As noted above, the outer surface of an articulating portion can, in some embodiments, be uninterrupted by any features formed thereon. In other embodiments, as illustrated in FIG. 7, one or more surface features can be formed on an outer surface of the articulating portion. Even if one or more such features are included, the outer surface 722 of the articulating portion 702 can remain sealed against fluid ingress. Furthermore, orienting such features longitudinally as shown can provide advantages over known configurations in which one or more slots, etc., are formed in a transverse or radial direction (e.g., relief slots or segmented sections). For example, the longitudinally-extending groove 720 can be less likely to get caught on tissue or other structure when, for example, advancing a surgical instrument toward a surgical site.

Figure 8:
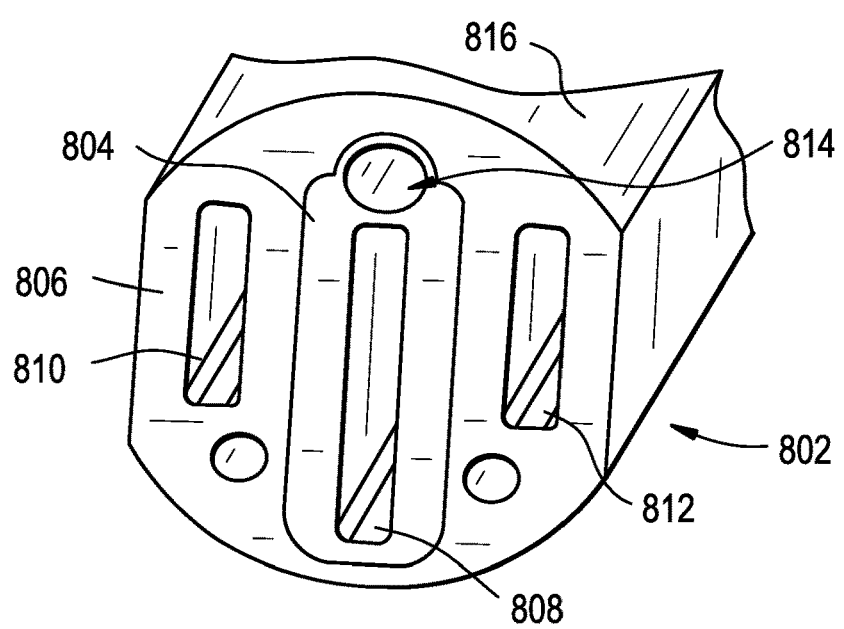
FIG. 8 is a perspective view of another embodiment of an articulating portion of a surgical instrument.

FIG. 8 illustrates a further alternative embodiment of an articulating portion 802. The articulating portion 802 can be similar to the articulating portions 502 and 702 in including an inner component 804, and outer component 806, a first lumen 808 formed in the inner component 804 that can receive a cutting element therein, and second and third lumens 810, 812 formed in the outer component 806 that can receive articulation control bands therein. In the embodiment of FIG. 8, however, a fourth lumen 814 can be formed in the inner component 804, in contrast to the fourth lumen 714 formed in the outer component 706 shown in FIG. 7. As noted above, the fourth lumen 714 can be configured to receive a conductor for delivering electrical energy in some embodiments, or one or more actuating elements that can be configured to, for example, open and close jaw members of an end effector. Forming the fourth lumen 814 in the more rigid material utilized to form the inner component 804 can provide increased protection and support for any cable, wire, or other component received therein. In other embodiments, any number of other lumens can be formed in any of the inner component 804 and the outer component 806.

FIG. 8 also illustrates a further embodiment of an outer surface 816 of the articulating portion 802. In particular, the outer surface 816 can be uninterrupted without any surface features formed thereon (e.g., there is no groove 720 formed therein) and its circular cross-sectional shape can be truncated by opposed flat sides. Such a configuration can save space in some embodiments when compared, for example, to the circular cross-section of the articulating portion 502 shown in FIG. 6. Still further, the opposed flat sides can facilitate articulation in some embodiments, as it can be easier to bend the articulating portion 802 against one of the opposed flat sides as compared to the convex shape of the upper and lower curved surfaces.

Figure 9:
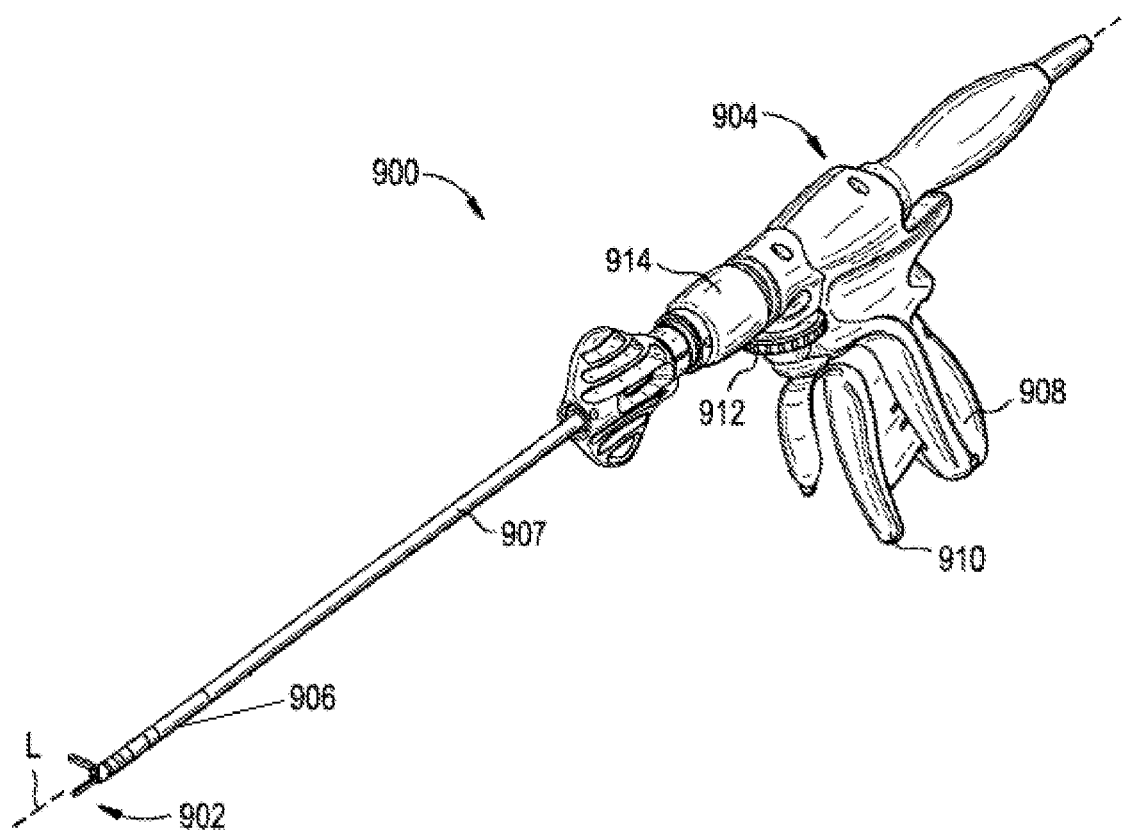
FIG. 9 is a perspective view of one embodiment of an articulating surgical instrument.

As noted above, in some embodiments the surgical instrument can be configured to deliver tissue transection and/or sealing energy via ultrasound, as opposed to, for example, electrical energy. FIG. 9 illustrates one embodiment of a harmonic, or ultrasound, instrument/device 900. Similar to the electrosurgical instrument 10 described above, the instrument 900 can include a distal end effector 902 configured to grasp, transect, and seal tissue, a proximal actuating portion 904 configured to control operation of the end effector, an articulating portion 906 disposed between the end effector and the proximal actuating portion, and a shaft 907 extending distally from the proximal actuating portion.

As with the electrosurgical instrument 10, the proximal actuating portion 904 of the instrument 900 can be configured to interface with a human operator or a surgical robot via any of a variety of interface configurations. In the illustrated embodiment, the proximal actuating portion 904 can include a pistol grip 908 and first trigger 910 that can be configured to actuate the end effector to grasp tissue. The proximal actuating portion 904 can further include a second trigger 912 that can control delivery of ultrasonic energy to an oscillating cutting/sealing element of the end effector. As in the illustrated embodiment, the second trigger 912 can be a rotary dial that activates and modulates the amount of energy delivered to tissue. In other embodiments, other forms of a trigger can be utilized, including, for example, any of a variety of switches, buttons, levers, etc. Furthermore, the proximal actuating portion 904 can include a rotation control knob 914 that can be used to rotate any of the end effector 902, the articulating portion 906, and the shaft 907 relative to the proximal actuating portion 904 about a central longitudinal axis L extending through the shaft 907.

Figure 10:
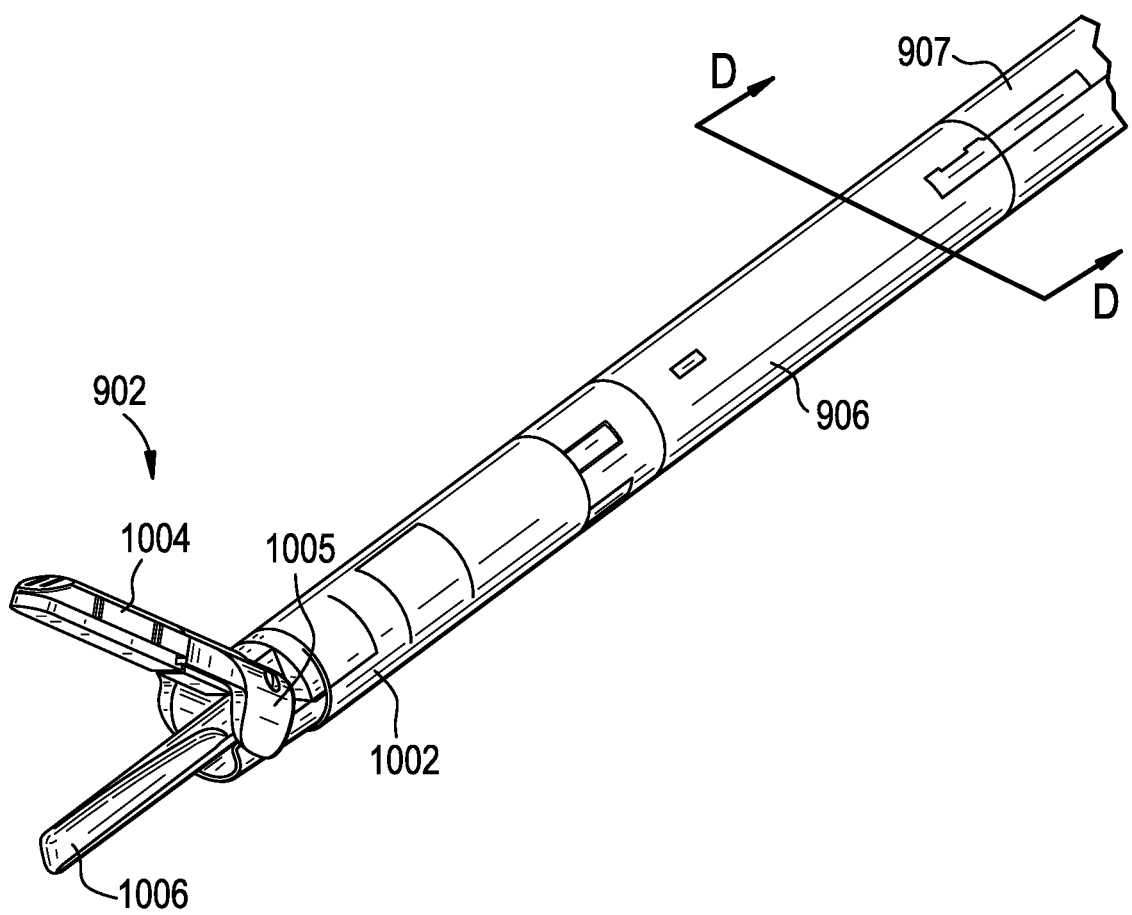
FIG. 10 is a detail view of a distal portion of the instrument of FIG. 9.

FIG. 10 illustrates a detail view of the end effector 902 of the harmonic instrument 900. The end effector 902 can be coupled to a distal end of the articulating portion 906, which can itself be coupled to a distal end of the shaft 907 that extends from the proximal actuating portion 904. The end effector 902 can include a rigid shaft portion 1002 that has a first jaw member 1004 pivotably coupled thereto via pivot pin 1005. An oscillating cutting/sealing element 1006 can extend from the shaft 1002 and can function as a second jaw member such that the end effector can be configured to grasp tissue between the first jaw member 1004 and the cutting element 1006. Actuation of the first jaw member 1004 can be accomplished using one or more actuating members that extend from the end effector 902 back to, for example, the first trigger 910 of the proximal actuating portion 904.

In use, one or more layers of tissue can be disposed between the cutting element 1006 and the first jaw member 1004 when in the open configuration shown in FIG. 10. A user or surgical robot can then cause the first jaw member 1004 to pivot toward the cutting element 1006 about the pivot pin 1005 to clamp the tissue therebetween. Finally, ultrasonic energy can be delivered to the grasped tissue by rapidly oscillating the cutting element 1006 such that the cutting element 1006 transects and seals the grasped layers of tissue, as described above.

Figure 11:
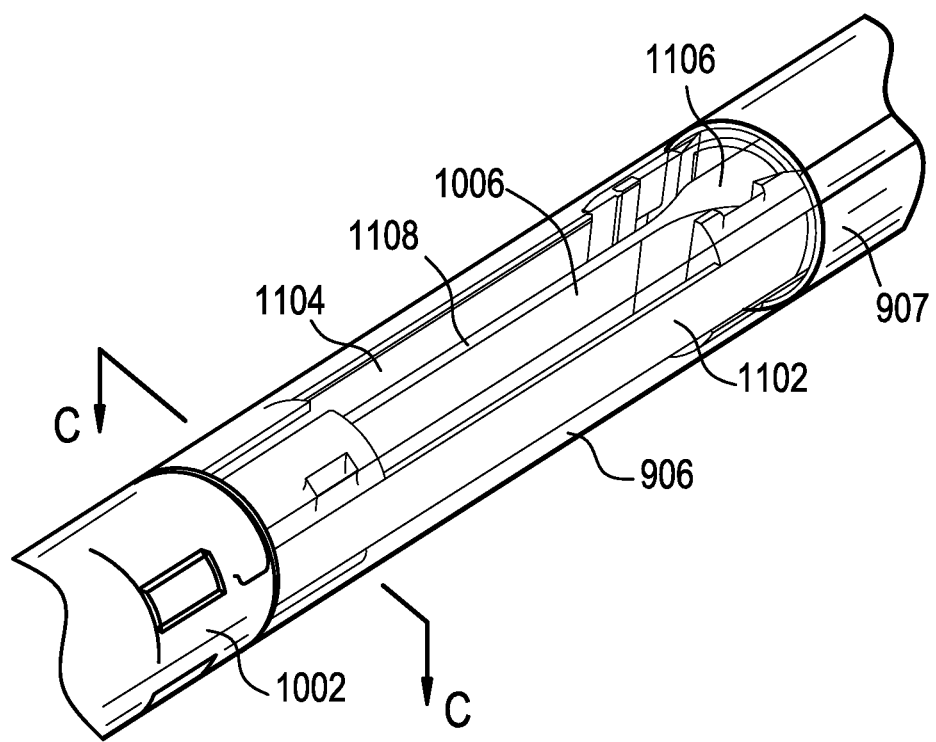
FIG. 11 is a partially transparent detail view of the articulating portion of the instrument of FIG. 9.
Figure 12:
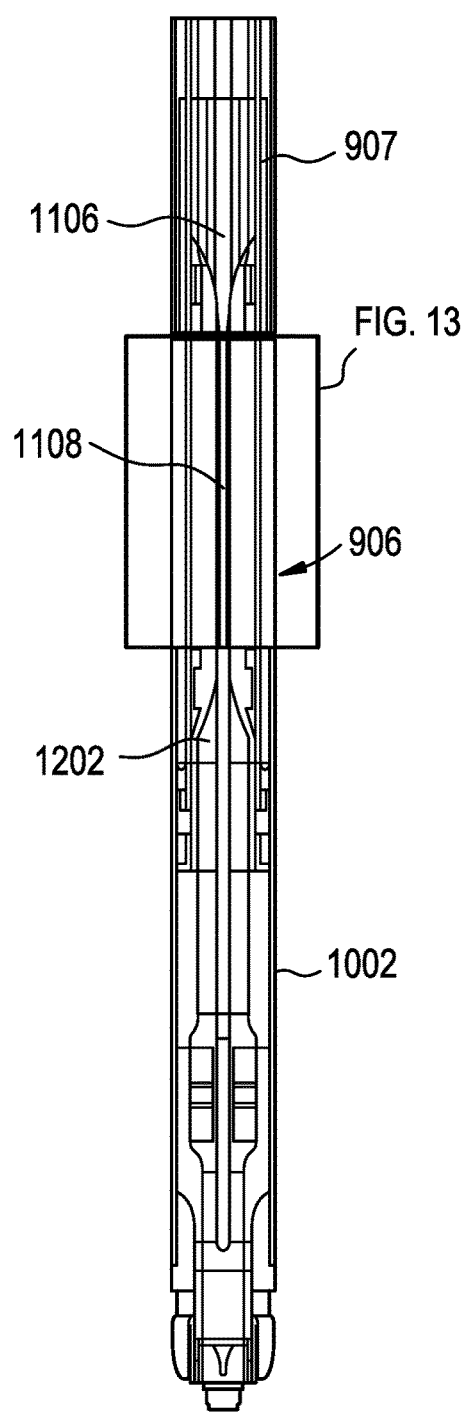
FIG. 12 is a top cross-sectional view, taken along the line C-C shown in FIG. 11, of the distal portion of the instrument of FIG. 9.
Figure 13:
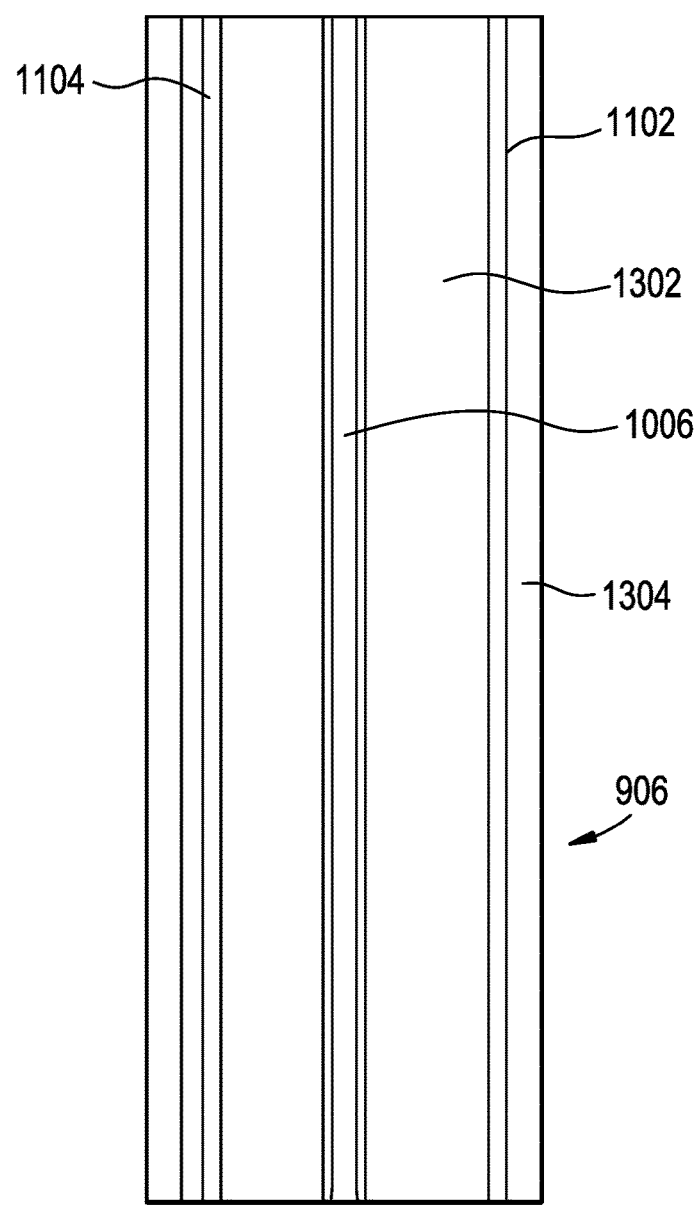
FIG. 13 is a detail view of the top cross-sectional view of the articulating portion of the instrument of FIG. 12.

The instrument 900 can include an articulating portion 906 that can be similar to the articulating portions 502, 702, 802 described above. As shown in FIGS. 11-14, the articulating portion 906 can be formed from one or more elastically deformable materials. In one embodiment, the articulating portion 906 can be formed by coextruding an inner component 1302 and an outer component 1304 such that the outer component surrounds the inner component, as shown in FIG. 13. As described above, the inner component can be more rigid, e.g., have a higher modulus of elasticity, than the outer component. Further, the articulating portion 906 can include one or more lumens formed therein. For example, the articulating portion 906 can include a first lumen configured to receive the cutting/sealing element 1006, as well as a second lumen configured to receive a first articulation control band 1102 and a third lumen configured to receive a second articulation control band 1104.

In some embodiments, the cutting/sealing element 1006 can have a different cross-sectional profile as it passes through the articulating portion 906 compared to a cross-sectional profile proximal and/or distal thereto. For example and as shown in FIG. 11, the cutting/sealing element 1006 can taper or "neck down" from a first cross-sectional shape at position 1106 that is proximal to the articulating portion 906 to a second cross-sectional shape at position 1108 inside the articulating portion. The second cross-sectional shape 1108 can be narrowed in at least one dimension compared to the first cross-sectional shape 1106, which can reduce the space required within the articulating portion 906. Further, if the cutting element 1006 is narrowed in the manner shown in FIG. 11, wherein a width of the cutting element extending between the first and second articulation control bands 1102, 1104 is reduced, it can better facilitate articulation of the cutting element 1006 toward or away from the articulation control bands. In some embodiments, the cutting element 1006 can return to the first cross-sectional shape at a position 1202 that is distal to the articulating portion 906, as shown in FIG. 12. Of course, in some embodiments the cutting element 1006 can transition from the second cross-sectional shape at position 1108 to a different third cross-sectional shape at the position 1202.

Figure 14:
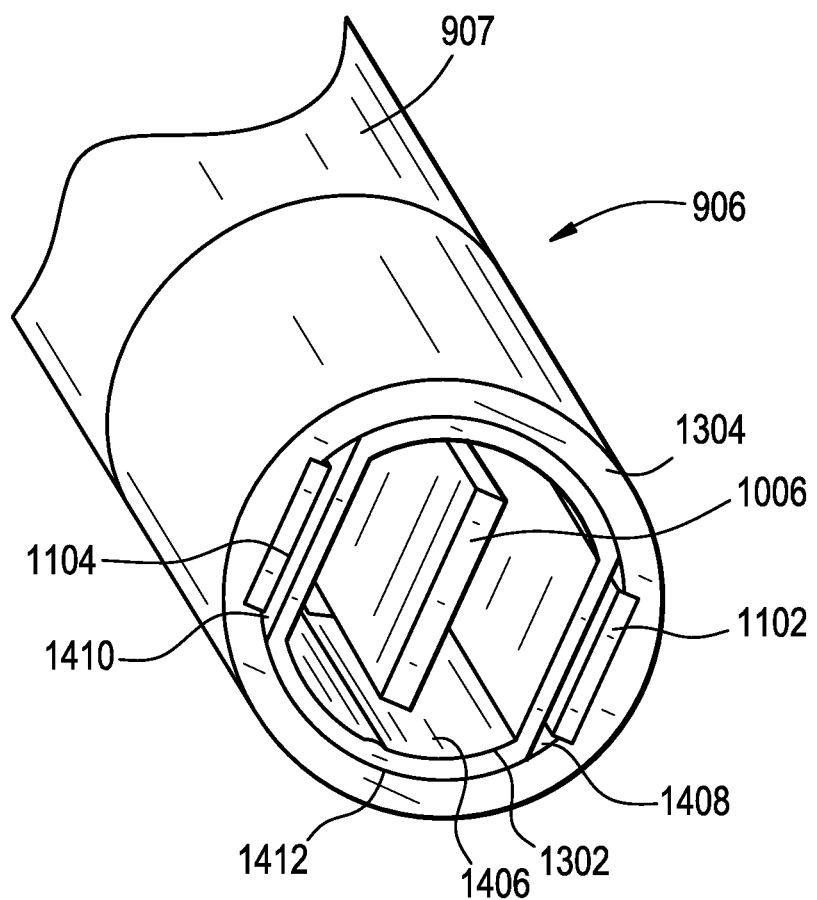
FIG. 14 is a perspective cross-sectional view, taken along the line D-D shown in FIG. 10, of the articulating portion of the instrument of FIG. 9.

FIG. 14 illustrates an end cross-sectional view of the articulating portion 906, exposing the arrangement of the various components described herein. In this view, the inner component 1302 can be seen surrounded by the outer component 1304 of the articulating portion 906. The inner component 1302 can include a lumen 1406 formed therein to accommodate the cutting element 1006. The lumen 1406 can be significantly larger in cross-sectional area than the cutting element 1006 in order to provide clearance around the cutting element for ultrasonic vibration during use. Forming the lumen 1406 in the manner of the above-described lumens that are of substantially the same cross-sectional area as the components received therein can interfere with transmission of ultrasonic energy in certain embodiments. This is because the inner component 1302 can serve as a damper that absorbs ultrasonic energy if the cutting element 1006 contacts the wall of the inner component 1302 during operation.

In the illustrated embodiment of FIG. 14, the inner component 1302 can be formed with flat sides and the outer component 1304 can be formed with a circular profile, thereby creating symmetrically opposed recesses 1408, 1410 that can be configured to receive the articulation control elements 1102, 1104. Further, one or more additional lumens, such as lumen 1412, can be formed through any of the inner component 1302 and the outer component 1304 to receive, for example, an actuating cable, rod, band, etc. that can be used to control opening and closing of the first jaw member 1004, carry sensor data, etc.

Figure 15:
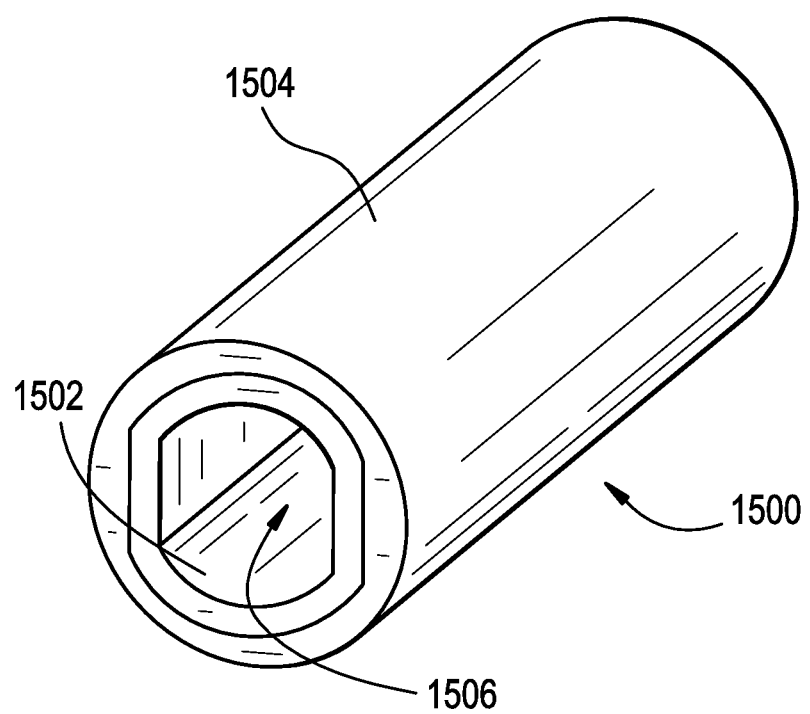
FIG. 15 is a perspective view of another embodiment of an articulating portion of a surgical instrument.

FIG. 15 illustrates an alternative embodiment of an articulating portion 1500 that can be utilized in connection with the surgical instruments described herein, e.g., ultrasonic surgical instrument 900. The articulating portion 1500 can include an inner component 1502 formed from a first material and an outer component 1504 formed from a second material. As with other embodiments described herein, the first material of the inner component can have a higher modulus of elasticity than the second material of the outer component, such that the articulating portion can selectively deform while maintain a straight configuration (as illustrated) in the absence of a force imparted by, for example, an articulation control element such as a band, cable, or rod extending through the articulating portion from an end effector to a proximal actuating portion. In the embodiment of FIG. 15, the inner component 1502 can include a single central lumen 1506 that can be configured to receive a cutting/sealing element and one or more articulation control bands. Accordingly, in some embodiments a single lumen can house all components extending from the end effector to the proximal actuating portion. Of course, in other embodiments any number of different lumens formed in any of the inner component 1502 and the outer component 1504 can be utilized.

Figure 16:
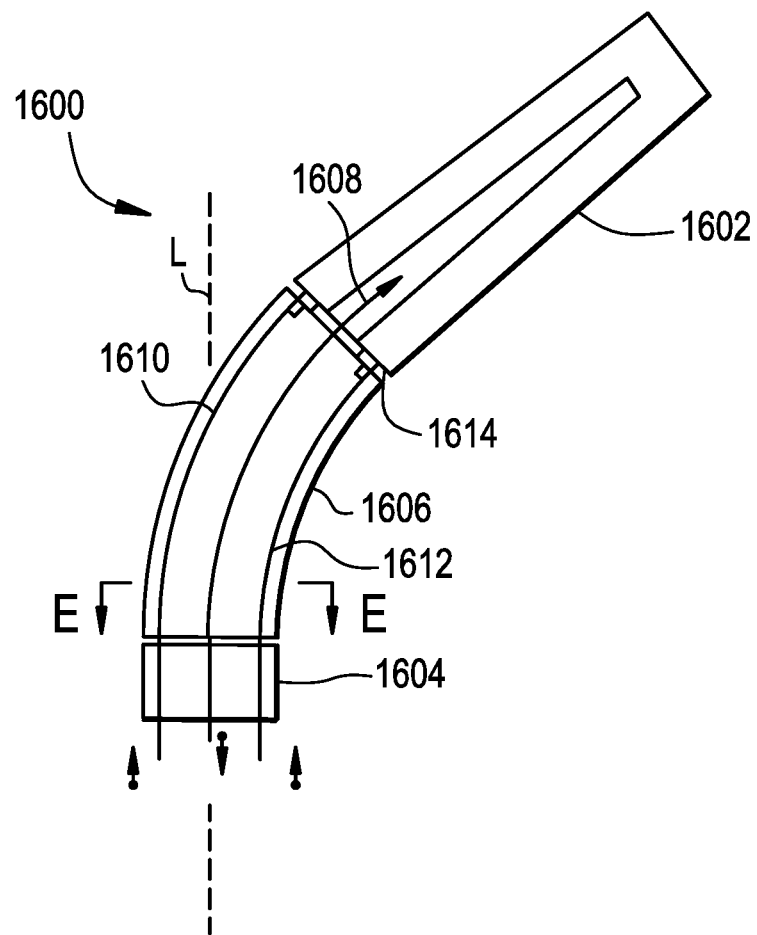
FIG. 16 is a top view schematic of one embodiment of a distal portion of a surgical instrument including an end effector and an articulating portion.

FIG. 16 illustrates still another embodiment of an articulating portion 1606 that can be disposed between a distal end effector 1602 and a shaft 1604 extending from a proximal actuating portion (not shown) of a surgical instrument 1600. The end effector 1602 can include a cutting element 1608 disposed therein that can be utilized to transect tissue grasped by the end effector. The cutting element 1608 can extend, or be coupled to another element that extends, proximally out of the end effector 1602, through the articulating portion 1606, and back to the proximal actuating portion (not shown). The cutting element 1608 can be configured to translate proximally and distally relative to the end effector 1602 in order to transect grasped tissue.

The instrument 1600 can also include one or more articulation control elements that can be configured to distally extend or proximally retract in order to urge the end effector 1602 in a direction transverse to a longitudinal axis L of the instrument. For example, in the top view of FIG. 16, the end effector 1602 is shown in an articulated configuration in which the end effector has been urged away from the longitudinal axis L of the instrument 1600 (to the right in the plane of the figure). The illustrated embodiment includes a first articulation control element 1610 and a second articulation control element 1612 that can each be coupled to the end effector and can extend through the articulating portion 1606 back to the proximal actuating portion (not shown). The illustrated articulation can be caused, for example, by distally extending or holding still the first articulation control element 1610 while proximally retracting the second articulation control element 1612.

The articulating portion 1606 of the instrument 1600 can be formed from multiple components as described above in some embodiments, but in other embodiments can be formed as a single monolithic component from a single material. The articulating portion 1606 can include a plurality of lumens formed therein to accommodate, for example, the cutting element 1608 and articulation control elements 1610, 1612. A variety of materials can be utilized for form the articulating portion 1606 and, in some embodiments, the articulating portion 1606 can be formed from silicone or another soft durometer elastomer material. In some embodiments, the first component 1606 can be formed from a material having a Shore A durometer approximately in the range of about 70 and about 80.

The articulating portion 1606 formed from such a material can be less rigid than the above-described embodiments in which a more rigid first material and a more flexible second material are coextruded, molded, or otherwise produced to create an articulating portion with an inner component and an outer component. In some embodiments, use of a less rigid articulating portion 1606 can be accomplished because the articulation control elements 1610, 1612 can be configured to carry all tensile loads created by the cutting element 1608. In such embodiments, no tensile load is carried by the articulating portion, thereby reducing the need for rigidity in the material used to create the articulating portion 1606. Articulating portion 1606 can provide advantages over known designs, e.g., known devices that utilize a series of segmented beads or sections that move relative to one another. For example, the monolithic articulating portion 1606 formed from an elastomer can provide for similar articulation performance, but can be less prone to unintended articulation or change in curvature during maneuvers that produce compressive loading, such as dissection, poking, prodding, etc.

In order to effectively transfer all tensile loads from the cutting element 1608 to the articulation control elements 1610, 1612, it can be desirable to include at least two articulation control elements and to position the articulation control elements on opposite sides of the cutting element. Further, it can be desirable to maintain a parallel orientation of the cutting element 1608 and the articulation control elements 1610, 1612. This can be accomplished in some embodiments by including a gusset 1614 formed at a proximal end of the end effector 1602 that can ensure the articulation control elements 1610, 1612 extend perpendicularly away from the end effector 1602. The gusset 1614 can have a variety of shapes and sizes, including, for example, a substantially "L"-shaped bracket, an annular "L"-shaped ring, and other known designs.

Further, the gusset 1614 can also serve as a feature that can engage the articulating portion 1606. For example, the articulating portion 1606 can include one or more recesses formed therein that can be configured to receive a portion of the gusset 1614 therein when assembled. In such an embodiment, the gusset 1614 and one or more recesses formed in the articulating portion 1606 can serve as locating features and can resist relative rotation or movement between the end effector 1602 and the articulating portion 1606 during use, similar to the recesses or lumens 716, 718 described above.

Figure 17:
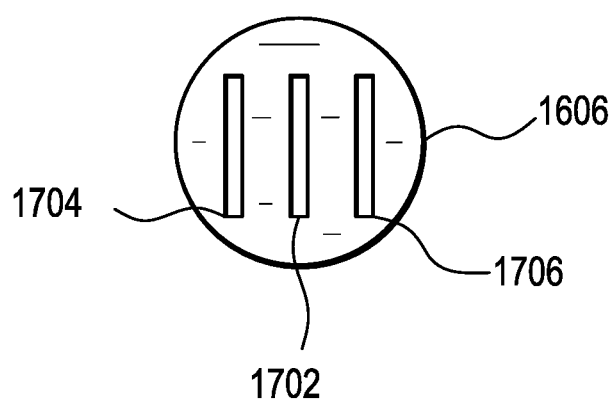
FIG. 17 is a front cross-sectional view, taken along the line E-E shown in FIG. 16, of the articulating portion of the instrument of FIG. 16.

FIG. 17 illustrates an end view of the articulating portion 1606. As illustrated, the articulating portion 1606 can include a plurality of lumens formed therein that can be configured to receive the cutting element 1608 and articulation control elements 1610, 1612. For example, the articulating portion 1606 can include a first lumen 1702 configured to receive the cutting element 1608, a second lumen 1704 configured to receive the first articulation control element 1610, and a third lumen 1706 configured to receive the second articulation control element 1612. In other embodiments, additional lumens can also be included, for example, to carry a conductor for delivering electrical energy or another actuating cable, rod, etc.

In some embodiments, the lumens 1702, 1704, 1706 can be configured to precisely locate the components carried therewithin so as to avoid excess play that can make the end effector feel loose or flimsy during use. To accomplish this, the plurality of lumens 1702, 1704, 1706 formed in the articulating portion 1606 can each have a shape and a cross-sectional area that are substantially the same as a shape and a cross-sectional area of one of the plurality of articulation control elements 1610 or the cutting element 1608. In certain embodiments, proximal and distal translation of the components received within the lumens 1702, 1704, 1706 can be facilitated by lubricating the lumens or the components. Exemplary lubricants can include silicone and sodium stearate, though others are possible as well.

In addition to the above-described surgical instruments, also contemplated are various methods of utilizing these and other instruments that employ articulating portions according to the teachings provided herein. Such methods can include, for example, introducing any of the above-described instruments or devices into a patient's body, passively or actively articulating an end effector to access a surgical site, as well as grasping, sealing, and transecting tissue. Also contemplated are methods of producing the articulating portions described herein, including, for example, processes of co-extrusion and over-molding that can be utilized to form articulating portions having an inner component formed from a first material and an outer component formed from a second material.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present disclosure.

The instruments described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the instrument due to the materials utilized, the presence of electrical components, etc.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A surgical instrument, comprising:
   a distal end effector;
   a proximal actuating portion;
   an articulating portion disposed between the end effector and the actuating portion, the articulating portion having an inner component formed of a first material and an outer component formed of a second material that surrounds the inner component such that an outer surface defining outer sidewalls of the inner component is completely enveloped by the outer component; and
   an articulation control element that extends through a lumen of the outer component and that does not extend through an interior of the inner component, the articulation control element being configured to be actuated using the proximal actuating portion to articulate the distal end effector,
   wherein a modulus of elasticity of the first material is higher than a modulus of elasticity of the second material.

2. The instrument of claim 1, further comprising a cutting element disposed within another lumen of the articulating portion.

3. The instrument of claim 2, wherein the cutting element is configured to translate proximally and distally relative to the articulating portion.

4. The instrument of claim 2, wherein the cutting element is configured to pass through tissue via ultrasonic vibration.

5. The instrument of claim 1, wherein the distal end effector includes first and second jaw members movable relative to one another between an open position and a closed position to clamp tissue therebetween.

6. The instrument of claim 1, wherein the articulating portion includes a plurality of lumens formed therein.

7. The instrument of claim 6, wherein at least a first of the plurality of lumens is formed in the inner component of the articulating portion.

8. The instrument of claim 7, wherein at least a second of the plurality of lumens is formed in the outer component of the articulating portion.

9. The instrument of claim 8, further comprising a cutting element disposed within the lumen of the inner component.

10. The instrument of claim 1, wherein the modulus of elasticity of the inner component is approximately in a range of about 100 ksi and about 600 ksi.

11. The instrument of claim 1, wherein the modulus of elasticity of the outer component is approximately in a range of about 1 ksi and about 100 ksi.

12. The instrument of claim 1, wherein the outer component has an uninterrupted outer surface.

13. The instrument of claim 1, wherein the first material is any of nylon, polyetherimide, and polycarbonate.

14. The instrument of claim 1, wherein the second material is any of silicone, urethane, and polytetrafluoroethylene.

15. A surgical instrument, comprising:
    an end effector;
    a shaft; and
    an articulating portion disposed between the end effector and the shaft, the articulating portion having an inner component formed of a first material and an outer component formed of a second material that surrounds the inner component, wherein:
    a modulus of elasticity of the first material is higher than a modulus of elasticity of the second material;
    the articulating portion includes a first lumen formed in and fully enclosed by walls of the inner component, the first lumen having a cutting element disposed therein, the cutting element being configured to move relative to the inner and outer components to cut tissue grasped by the end effector; and
    the articulating portion includes a second lumen extending through the outer component but not the inner component, the second lumen having an articulation control element disposed therein, the articulation control element being configured to move relative to the inner and outer components to articulate the end effector relative to the shaft.

16. The instrument of claim 15, wherein the second lumen includes two lumens and the articulation control element includes two articulation control elements such that each of the two lumens has one of the two articulation control elements disposed therein.

17. The instrument of claim 16, wherein the articulating portion includes a fourth lumen extending through the outer component but not the inner component, the fourth lumen having disposed therein either a conductor configured to deliver electrical energy to the end effector or a cable that is configured to move relative to the inner and outer components to move the end effector between an open position and a closed position.

18. The instrument of claim 15, wherein the modulus of elasticity of the inner component is approximately in a range of about 100 ksi and about 600 ksi.

19. The instrument of claim 15, wherein the modulus of elasticity of the outer component is approximately in a range of about 1 ksi and about 100 ksi.

20. The instrument of claim 15, wherein the first material is any of nylon, polyetherimide, and polycarbonate, and the second material is any of silicone, urethane, and polytetrafluoroethylene.

* * * * *